(12) United States Patent
Reitman et al.

(10) Patent No.: US 6,461,162 B1
(45) Date of Patent: Oct. 8, 2002

(54) METHOD FOR CREATION OF A CENTER FOR ATHLETIC PERFORMANCE ENHANCEMENT

(76) Inventors: Harold Reitman, P.O. Box 16328, Plantation, FL (US) 33318; Denise Bench, 3128 NW. 95th Ave., Coral Springs, FL (US) 33065; Ian B. Pyka, 102 NE. 2nd St., Suite 256, Boca Raton, FL (US) 33432

( * ) Notice: Subject to any disclaimer, the term of this patent is extended or adjusted under 35 U.S.C. 154(b) by 21 days.

(21) Appl. No.: 09/585,784

(22) Filed: Jun. 5, 2000

(51) Int. Cl.$^7$ .............................................. A63B 69/00
(52) U.S. Cl. .................... 434/247; 434/257; 434/118; 434/262
(58) Field of Search ................................. 434/107, 247, 434/248, 251, 252, 253, 254, 256, 257, 262, 265, 118

(56) References Cited

U.S. PATENT DOCUMENTS

| | | | |
|---|---|---|---|
| 4,839,822 A | 6/1989 | Dormond et al. | 364/513 |
| 4,847,784 A | 7/1989 | Clancey | 364/513 |
| 5,486,001 A | * 1/1996 | Baker | 273/183.1 |
| 5,619,991 A | 4/1997 | Sloane | 128/630 |
| 5,722,418 A | 3/1998 | Bro | 128/732 |
| 5,819,267 A | 10/1998 | Uyama | 707/6 |
| 5,835,683 A | 11/1998 | Corella et al. | 395/75 |
| 5,862,223 A | 1/1999 | Walker et al. | 380/25 |
| 5,908,383 A | 6/1999 | Brynjestad | 600/300 |
| 5,911,136 A | 6/1999 | Atkins | 705/36 |
| 5,954,510 A | 9/1999 | Merrill et al. | 434/236 |
| 6,026,148 A | 2/2000 | Dworkin et al. | 379/88.18 |
| 6,050,924 A | 4/2000 | Shea | 482/57 |
| 6,126,596 A | 10/2000 | Freedman | 600/300 |
| 6,159,131 A | 12/2000 | Pfeffer | 482/8 |
| 6,171,218 B1 | 1/2001 | Shea | 482/57 |
| 6,208,974 B1 | 3/2001 | Campbell et al. | 705/3 |
| 6,223,165 B1 | 4/2001 | Lauffer | 705/8 |
| 6,249,809 B1 | 7/2001 | Bro | 709/217 |

OTHER PUBLICATIONS www.webmd.com, Unknown, See web site.
www.mvp.com, Unknown, See web site.
www.efit.com, Unknown, See web site.
"Interface Design Issue for Advice–Giving Expert Systems." John M. Carroll and Jean McKendree. *Communications of the ACM*, vol. 30 No. 1, (Jan. 1987), 14–31.

* cited by examiner

*Primary Examiner*—Kien T. Nguyen
(74) *Attorney, Agent, or Firm*—Ernest D. Buff; Ernest D. Buff & Associates LLC

(57) ABSTRACT

Persons engaged in physical activities, including athletic contests and attempts to reach peak physical performance in specific physical endeavors, are assisted by a coordinated database of relevant information derived from a staff of professionals who have the ability to interact with the participants in a globalized computerized network.

16 Claims, 4 Drawing Sheets

| Web site Home Page |
| Links and categories |

25      Home / Site Map / Profile / Notebook

21    Concept Statement – Message from our Founders

22    Mission Statement what the enhancement of athletic performance is all about 23    About our Company – Meet the Staff – Biographies – Certifications – Accolades 23    Feedback - a link which allows the user to post information about the website, (what they like, don't like)

23    Ask our Experts – a link which allows the user to directly access our team of experts with a question 24    Our areas of expertise : Sports Medicine, Sports Nutrition, Sport Injury Rehabilitation, Strength and Conditioning will be tailored with specific details relating directly to a specific sport. (Baseball, Football, Hockey, etc). The layout of the home page will be dedicated to this information. For an example of the grid, see *Figure 3b*.

24    Chatroom - which will be hosted by any member of our team of experts or by a celebrity spokesperson 24    Links to related services and websites 24    Products – manuals, merchandise Disclaimer notice, Secure site notice

METHOD FOR CREATION OF A CENTER FOR ATHLETIC PERFORMANCE ENHANCEMENT

BACKGROUND OF THE INVENTION

1. Field Of The Invention

This invention relates to methods by which a team of consultants, comprised of doctors, coaches, therapists, nutritionists, trainers, physiologists, psychologists and athletes, assist individuals engaged in athletic endeavors and physical activity in their attempt to maximize performance in these activities. More particularly, the methods use a global computerized network to create a "one stop shop" bringing together all of the aforementioned consultants to effectuate physical performance enhancement.

2. Description Of The Prior Art

Coaches train athletes in the specific skills for participation in a specific physical activity. In some, but not all cases, the coach may enlist the assistance of others in this endeavor. For example, the coach may refer the athlete to a specific subcategory of coach known as a strength-and-conditioning coach or to another subcategory of coach known as an exercise coach. This referral is designed to attempt to enhance the athlete's basic physical skills. The higher the level of competition, the more likely an athletic participant will have access to other specialists including, but not limited to nutritionists, exercise physiologists, and psychologists. These professionals also aim to refine and optimize athletic performance through a myriad of non-physical means within their specific area of expertise.

Without doubt, the most important asset for one participating in athletic endeavors or physical conditioning is the human body and its component parts. When injured, the injured party consults a medical doctor. The doctor may deploy any number of strategies designed to assist the injured party in obtaining the fastest and most effective recuperation as possible. Undoubtedly, any course of treatment will involve some type of diagnostic testing to assess the injury. Following injury assessment, the road to recovery may involve (among other things) prescription of some type of medication or, with severe situations, surgery to treat the injury. The goal in each instance is to return the injured patient to the pre-injury performance level as quickly as possible. As part of this process, the doctor may also refer the recovering patient to a physical therapist for rehabilitative instruction including, but not limited to, assistance with the performance of stretches and re-establishment of aerobic or anaerobic conditioning. A nutritionist may also be consulted to ensure a proper diet for recovery and return to pre-injury performance levels.

In recent years, web-based enterprises have attempted to make portions of a team approach to athletic performance available to the common athlete. For example, eFIT The Online Health and Fitness Network (www.efit.com) provides information on subjects relating to weight loss, nutrition, exercise and fitness. eFIT focuses on providing information regarding a narrow range of physical activities, such as cardio-fitness, strength training, cycling, running, hiking and walking, rather than taking a broad approach to physical activity. eFIT offers no expert interactive guidance in areas such as injury diagnosis, injury recovery and injury avoidance.

Healtheon/NWebMD (www.webmd.com) is an Internet healthcare company connecting consumers, doctors and the healthcare community. By linking consumers to a directory of physicians, live chat events and comprehensive healthcare information, Healtheon/WebMD offers advice on subjects relating to nutrition, injury diagnosis and injury recovery. Healtheon/NVebMD provides no interactive guidance on sports specific medicine or training.

MVP.com (www.mvp.com) is a source for athletic equipment and apparel on the Internet. MVP.com assists its users in the selection and purchase of athletic equipment, in the proper care for that equipment, interactive instructional guides on training and performance. The information on the MVP.com website is organized in a sport specific manner. MVP.com offers no interactive guidance on sports medicine, nutrition, injury diagnosis and injury recovery.

To insure optimum performance of the athlete, the activities of the various types of coaches (i.e. the strength-and-conditioning coach and the exercise coach), the nutritionist, the exercise physiologist, the psychologist, the doctor and the physical therapist, must be coordinated. However, even a coordinated, team approach to athletic performance enhancement is found, if at all, only at the highest levels of competition, such as in some professional sports, in some major college sports and among some Olympic athletes and then not often but still found interactively. Assembling such a team for the enhancement of athletic endeavors and physical activity is prohibitively expensive at any other level of competition and for the everyday individual engaged in athletic endeavors or physical activity.

SUMMARY OF THE INVENTION

The present invention relates to methods by which a team of consultants assists participants in athletic endeavors and physical activity attempting to enhance athletic performance. The team of consultants is comprised of doctors, coaches, therapists, nutritionists, trainers, physiologists, psychologists, and athletes. The assistance includes advice and counsel with regard to strength and conditioning exercises, nutrition, medicine and injury rehabilitation. The assistance is organized in an information database tailored to an individual athlete competing in a specific sport. The assistance is provided in an interactive networked computer environment. The information database is established on a first computer. An interface allows remote connection of the team to the first computer and the database. The members of the team inputs and updates the information database. The interface also allows remote access to the database by one or more users. The users may query the database for specific topics and may simultaneously with to one or more members of the team. The interface also enables members of the team to interactively communicate with one another with the information provided to the user, thus creating the coordinated effort toward physical activity enhancement.

BRIEF DESCRIPTION OF THE DRAWINGS

The invention will be more fully understood and further advantages will become more apparent when reference is made to the accompanying drawings and the following detailed description of the preferred embodiments. While the discussion below incorporates verbiage that places the invention in the context of the Internet and the World Wide Web, the concept is equally applicable in a generalized network environment.

FIG. 2 is a schematic diagram of a website dedicated to the enhancement of physical activity performance, showing sections for site description, feedback, interactive communication between members of the team, between members of the team and the object user, and a sports information database;

DETAILED DESCRIPTION OF THE PREFERRED EMBODIMENTS

The present invention relates to methods by which a team of consultants assists athletes attempting to enhance athletic performance. The team of consultants is comprised of doctors, coaches, therapists, nutritionists, trainers, physiologists, psychologists, and athletes. The assistance includes advice and counsel with regard to exercises, nutrition, medicine and injury rehabilitation. The assistance is organized in a coordinated interactive information database that is tailored to an individuals participating in various physical activities.

Figure 1:
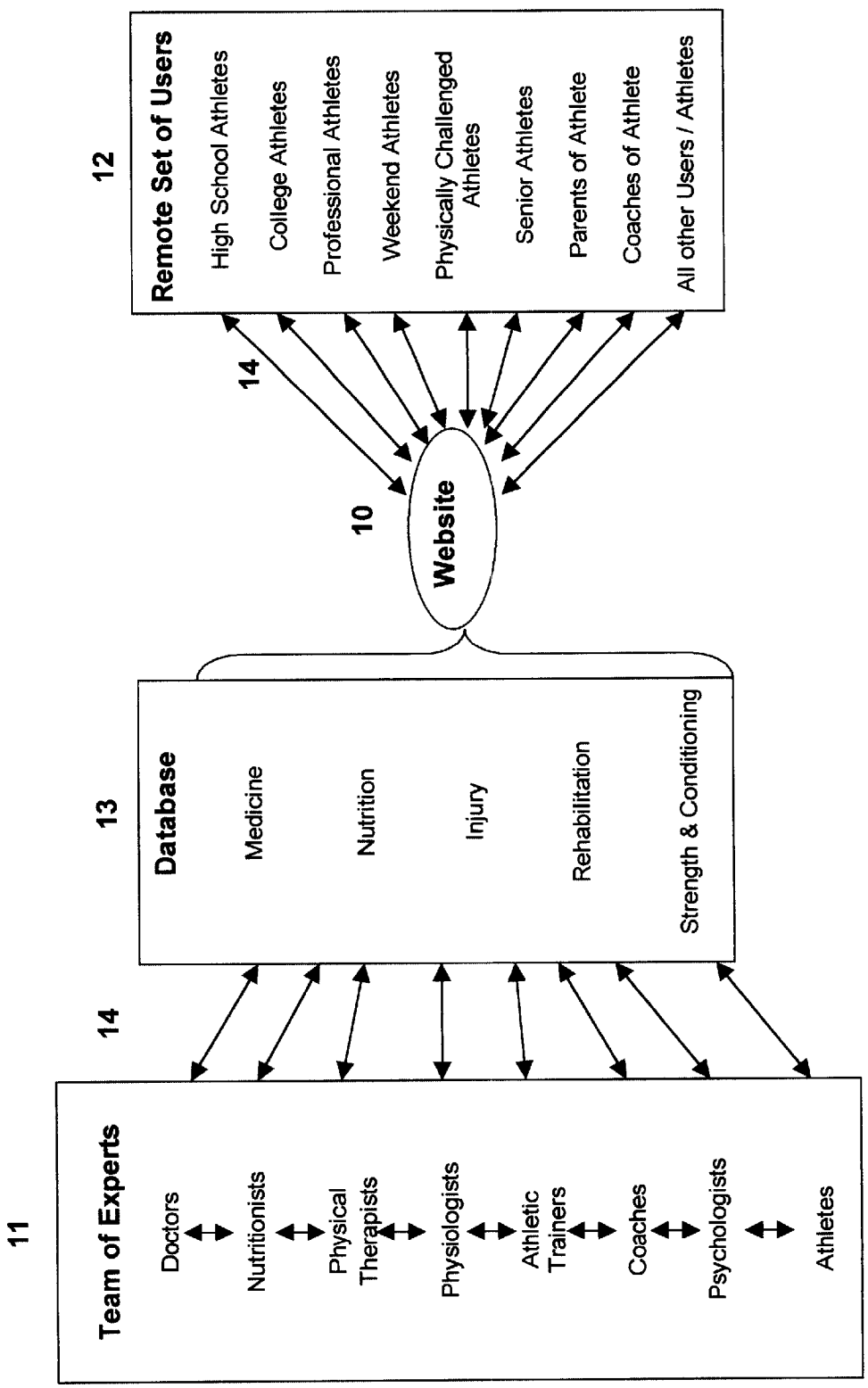
FIG. 1 is a schematic diagram of a computer network linking a remote team and a remote set of users through a website.

As illustrated by FIG. 1, the assistance described above is organized in an interactive networked computer environment or a website 10. A website is, in general terms, a server application that accepts connections from remote, user programs. User programs, such as web browsers, allow the remote user to access the information database stored on the website. Such an information database can include a broad range of multimedia data including textual, graphical, video, audio and animated information. The remote user typically navigates his way around the website via a mouse or keyboard.

In the present invention, remote users can either be members of the team 11 or users 12. The information database 13 is established on a first computer. An interface 14 allows remote connection of one or more members of the team 11 to the first computer and the database 13. The members of the team 11 input and update the information database 13. The interface 14 also allows remote access to the database 13 by one or more users 12. The users 12 may query the database 13 for specific topics and may interactively connect to one or more members of the team 11. The interface also enables members of the team 11 to communicate with one another with regard to the information provided to the user 12, thus creating the coordinated interactive effort toward performance enhancement.

FIG. 2 illustrates the website homepage. Once the user enters the website, a home page 20 is presented and a user profile will appear. The home page 20 describes the website, and includes a mission statement 21, information about the sponsoring organization 22, how to contact the website administrators and members of the team 23, and how the site will benefit the user in terms of products and services 24.

The homepage 20 will also direct the user to a user profile 25. The user profile 25 will consist of fields that are built into a relational database. The identified fields which are to be included on this profile 25 include, but are not limited to the following:

First Name

Last Name

Age

Location by City and State

Gender

Email address, and the choice of receiving graphics or text only

Level and type of activity/performance: high school, college, professional, weekend warrior, senior, physically challenged, other Top 3 activities of choice The area of activity performance enhancement most interested in (e.g. strength and conditioning, nutrition, medicine, injury rehabilitation)

Password

Upon further visits, the user and the user's choices, which were listed in the original profile, are known. Information pertaining to these choices is accessed from the database and presented to the athlete. The user has the ability to return to the entire database at any time and designate new selections.

A complete analysis and log file, which tracks the individual user, referrals describing how the atheleteluser navigated to the website, what the user viewed within the website, and referrals describing where the user goes from the website are compiled on a daily, weekly and monthly basis. This information is then useful for advertising, marketing and business development.

Figure 3A:
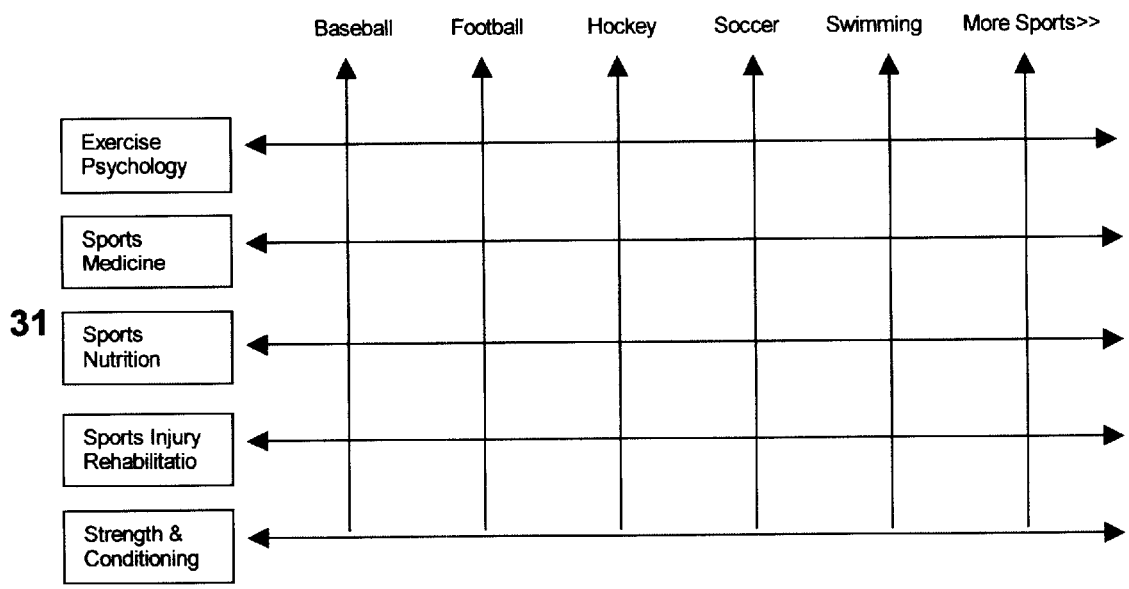
FIG. 3 is a schematic diagram of the sports information database section of the website, including illustrated sections for strength and conditioning, nutrition, medicine, injury rehabilitation, and exercise psychology linked to each specific sport.

As illustrated by FIG. 3a, the website presents the database in the form of a gridiron. Each column 30 of the gridiron is designated for a specific activity (e.g. hockey, football, soccer). Each row 31 of the gridiron is designated for a specific area of interest (e.g. strength and conditioning, nutrition, medicine, injury rehabilitation). Each intersection of a column 30 and row 31 represents the information in the database related to the specific area of interest linked to the specific activity.

Figure 3B:
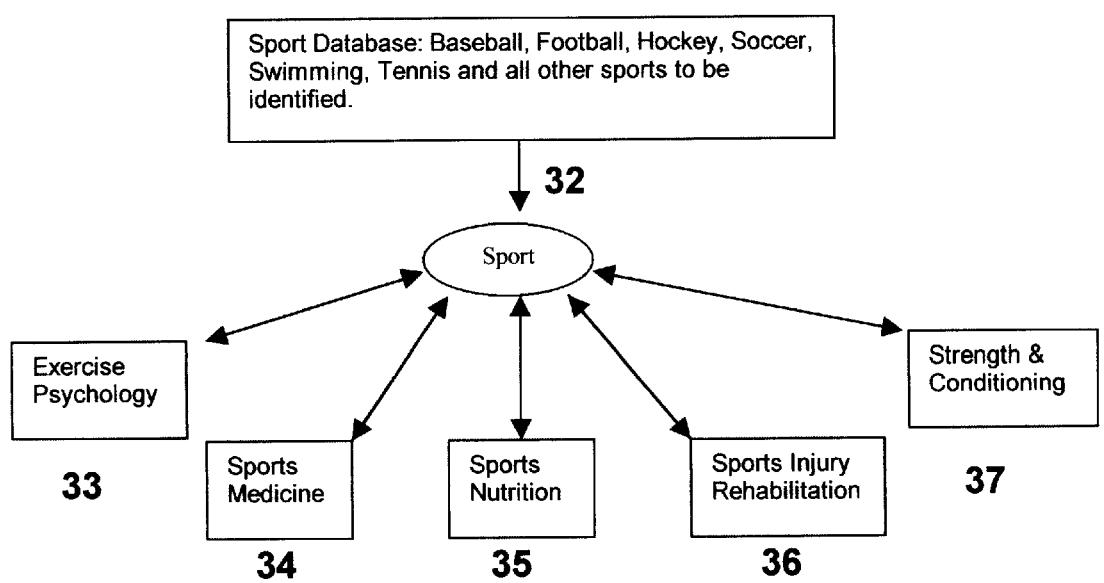

FIG. 3b depicts one column of the gridiron. The column is designated for a specific activity 32. The information database supporting that activity includes exercise psychology 33, medicine 34, nutrition 35, injury rehabilitation 36 and strength and conditioning 37.

As the user moves around the gridiron, the icon becomes selective to the activity to which they are pointing. For example, when in the football row, the icon is a football player running across the gridiron. In the soccer row, the icon is a player kicking a soccer ball into the appropriate area. Each area of the website can be accessed either through a specific activity or through the area of interest.

Figure 4:
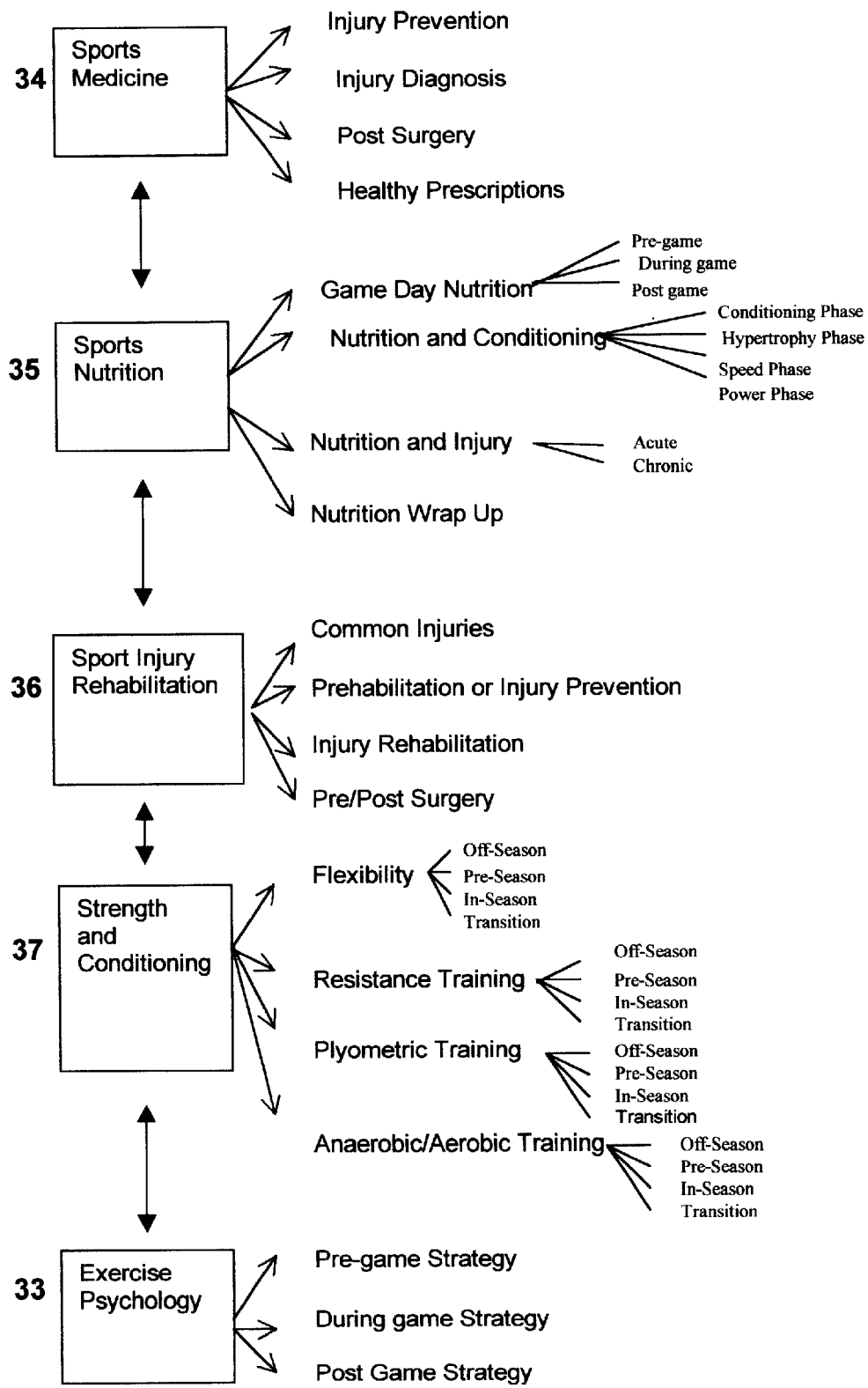
FIG. 4 is a schematic diagram of the sections for strength and conditioning, nutrition, medicine, injury rehabilitation, and exercise psychology for a specific activity.

FIG. 4 is a schematic diagram of the information contained in each specific area of interest for each specific activity.

Information on strength and conditioning 37 describes methodologies for improving the quality of joint and muscle activity in the context of the demands of specific activities. The information includes by way of example, but is not limited to, flexibility training, resistance training, plyometric training and anaerobic/aerobic training. The information is divided into sections describing pre-season, in-season, transition and off-season training regiments. The information is provided and maintained by a group of highly trained strength-andcoaches, physical therapists, trainers, physiologists, psychologists, from accredited organizations such as, but not limited to the National Strength and Conditioning Association, the American Physical Therapy Association, the National Athletic Trainers Association, and the Association for Advancement of Applied Sports Psychology.

Information on nutrition 35 describes the user's diet and the timing of the user's meals. The information includes, but is not limited to, activity day nutrition, nutrition and conditioning, and nutrition and injury. Activity day nutrition is divided into three subcategories; nutritional strategies before competing, nutritional strategies while in the act of competing, and nutritional strategies that help you recover from activity. Nutrition and conditioning is divided into four subcategories; nutrition during conditioning, nutrition during hypertrophy, nutritional strategies to increase speed, and nutritional strategies to increase power. Nutrition and recovery is divided into two subcategories; nutritional strategies for recovery from acute injuries and nutritional strategies for recovery from chronic injuries. This information is provided and maintained by a group of doctors and nutritionists from accredited organizations such as, but not limited to American Sports Medicine Institute.

Information on activity medicine 34 describes a medical science approach to the potential of injury in activity. The information includes, but is not limited to, descriptions of common injuries, precautionary measures for injury avoidance, injury diagnosis, injury treatment and post injury strategies. Injury treatment includes, but is not limited to, surgical and non-surgical techniques. This information is provided by a group of physicians from accredited organizations such as, but not limited to the American Academy of Orthopedic Surgeons, the American Orthopedic Society for Sports Medicine and the American Sports Medicine Institute.

Information on injury recovery 36 describes guidelines for the period after injury treatment. This period extends through rehabilitation, and includes the resumption of safe training and the return to activity. This information is provided by a group of physicians, therapists, certified trainers, coaches, physiologists and psychologists from accredited organizations such as, but not limited to the American Academy of Orthopedic Surgeons, the American Orthopedic Society for Sports Medicine, the American Sports Medicine Institute, the American Physical Therapy Association, the Association for Advancement of Applied Sports Psychology, and the National Athletic Trainers Association.

Having thus described the invention in rather full detail, it will be understood that such detail need not be strictly adhered to, but that additional changes and modifications may suggest themselves to one skilled in the art, all falling within the scope of the invention as defined by the subjoined claims.

What is claimed is:

1. A method for assisting participants attempting to reach peak performance in specific physical activities comprising:
   a. assembling a staff comprised of physicians, coaches, therapists, nutritionists, trainers, physiologists, psychologists, and athletes;
   b. establishing a coordinated database of relevant information provided by said staff;
   c. allowing user access to said coordinated database; and
   d. providing expert guidance to users of said coordinated database.

2. A method as recited by claim 1, wherein delivery of information to the user is provided in an interactive networked computer environment.

3. A method recited by claim 2, wherein:
   a. the coordinated database and a database interface is established on a first computer;
   b. the interface allows remote connection of one or more staff members to the first computer and the coordinated database;
   c. the interface allows remote access to the coordinated database by one or more users;
   d. the athlete queries the database to specify topics, staff members or topics and staff members; and
   e. the athlete interactively connects to one or more of the staff members as the staff members interactively connect to each other and the user.

4. A method as recited by claim 3, wherein the coordinated database is divided into sections specifically addressing specific sections related to activity enhancement including the following topics: a) strength and conditioning, b) nutrition, c) medicine, d) injury rehabilitation, and exercise psychology.

5. A method as recited by claim 4, comprising one or more of the following topics on strength and conditioning:
   a) Flexibility
   b) Resistance Training
   c) Plyometric training
   d) Anaerobic and aerobic training
   e) Pre-season conditioning
   f) In-season conditioning
   g) Post season conditioning.

6. A method as recited by claim 4, comprising one or more of the following topics on nutrition:
   a) Game day nutrition
   b) Nutrition and conditioning
   c) Nutrition and injury.

7. A method as recited by claim 4, comprising one or more of the following topics on medicine and injury rehabilitation:
   a) Common injuries
   b) Injury prevention
   c) Injury diagnosis
   d) Rehabilitation from injury
   e) Pre surgery conditioning
   f) Surgery and surgery options
   g) Post surgical rehabilitation
   h) Healthy prescriptions.

8. A method as recited by claim 3, wherein said remote user creates a user profile enabling the interface to direct the user to appropriate sections of the coordinated database matched to the user's interests.

9. A method as recited by claim 8, wherein the remote user creates a notebook in his/her user profile to save specific information.

10. A method as recited by claim 9, wherein the specific information is easily accessed and printed.

11. A method as recited by claim 8, wherein the staff can electronically interact with the user through the interactive coordinated database and provide advice to the user through the user profile, via electronic mail, or via communication vehicles outside the networked computer environment.

12. A method as recited by claim 11, wherein the staff acts as an interactive personal resource for the user.

13. A method as recited by claim 12, wherein;
   a. the staff creates a customized exercise plan for the user;
   b. the user records his/her exercise metrics; and
   c. the staff reviews the exercise metrics and makes necessary adjustments to the customized exercise plan.

14. A method as recited by claim 13, wherein the customized exercise plan, the training metrics and the adjustments to the customized exercise plan are exchanged through the interactive user profile, electronic mail or other communication vehicles.

15. A method as recited by claim 3, wherein the delivery of information via the interactive coordinated database includes a portion of the database devoted to instant communication dialogue between multiple users and staff or guests.

16. A method as recited by claim 3, wherein the interactive coordinated database provides electronic links for its users to other web sites containing related to activity performance enhancement information.

* * * * *